United States Patent
Larroux et al.

(10) Patent No.: US 9,970,889 B2
(45) Date of Patent: May 15, 2018

(54) ENERGY IMAGING WITH GENERALLY CONSTANT ENERGY SEPARATION

(71) Applicant: General Electric Company, Schenectady, NY (US)

(72) Inventors: Jean-Francois Larroux, Buc (FR); Julien Bouhraoua, Buc (FR); Aurelien Gadenne, Buc (FR); Uwe Wiedmann, Niskayuna, NY (US); Mark Frontera, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 526 days.

(21) Appl. No.: 14/658,913

(22) Filed: Mar. 16, 2015

(65) Prior Publication Data

US 2016/0192465 A1  Jun. 30, 2016

Related U.S. Application Data

(60) Provisional application No. 62/098,001, filed on Dec. 30, 2014.

(51) Int. Cl.
*G01N 23/04* (2006.01)
*H05G 1/58* (2006.01)
*A61B 6/03* (2006.01)
*A61B 6/00* (2006.01)

(52) U.S. Cl.
CPC ............. *G01N 23/046* (2013.01); *H05G 1/58* (2013.01); *A61B 6/032* (2013.01); *A61B 6/482* (2013.01)

(58) Field of Classification Search
CPC ...... G01N 23/046; A61B 6/032; A61B 6/482; H05G 1/32; H05G 1/58
See application file for complete search history.

(56) References Cited

U.S. PATENT DOCUMENTS

| 7,813,474 B2 | 10/2010 | Wu et al. |
| 8,031,831 B2 | 10/2011 | Zou |
| 8,189,741 B2 | 5/2012 | Ernest et al. |
| 8,755,491 B2 | 6/2014 | Rosevear et al. |
| 2012/0155613 A1* | 6/2012 | Caiafa ................. H02M 3/337 378/111 |

(Continued)

FOREIGN PATENT DOCUMENTS

| JP | 2013192801 A | 9/2013 |
| JP | 2014140528 A | 8/2014 |

OTHER PUBLICATIONS

Translation of JP 2013-192801 published in 2013.*

(Continued)

*Primary Examiner* — Glen Kao
*Assistant Examiner* — Chih-Cheng Kao
(74) *Attorney, Agent, or Firm* — Boyle Fredrickson, S.C.

(57) ABSTRACT

The present inventors have recognized that fall times between high-kV to low-kV levels (during a "dual energy" or "fast-kV" energy scan) are linked to the discharge of HV (high voltage) capacitance. In an embodiment of the invention, a high voltage generator may be activated during fall transitions from first to second energy levels in order to substantially maintain a predetermined fall transition time. Accordingly, substantially equal energy distributions between high-kV and low-kV levels may be achieved.

16 Claims, 4 Drawing Sheets

(56) References Cited

U.S. PATENT DOCUMENTS

| | | | |
|---|---|---|---|
| 2012/0155614 A1* | 6/2012 | Caiafa | H03K 3/53 378/111 |
| 2013/0251108 A1* | 9/2013 | Luerkens | H05G 1/10 378/106 |
| 2014/0205070 A1* | 7/2014 | Caiafa | H03K 17/04 378/101 |
| 2016/0192466 A1* | 6/2016 | Larroux | H05G 1/58 378/112 |

OTHER PUBLICATIONS

International Search Report and Written Opinion for corresponding PCT Appln. No. PCT/US2015/061637, dated Feb. 9, 2016, 11 pages.

* cited by examiner

ENERGY IMAGING WITH GENERALLY CONSTANT ENERGY SEPARATION

CROSS-REFERENCE(S) TO RELATED APPLICATION(S)

This application claims priority to U.S. Provisional Application No. 62/098,001, filed on Dec. 30, 2014, the disclosure of which is hereby incorporated by reference in its entirety.

BACKGROUND OF THE INVENTION

The invention relates generally to imaging systems, and more particularly to high voltage generators for imaging systems.

Computed Tomography (CT) is an X-ray medical imaging process which makes possible obtaining a three-dimensional (3D) image of a patient or object using a plurality of two-dimensional (2D) images acquired about the patient or object. In CT, dual energy imaging is known for obtaining material characterizations and/or reduction of artifacts by utilizing two scans of the patient or object at different voltage/energy levels, "low-kV" and "high-kV."

In a single rotation around the patient or object, a high voltage generator switches between "low-kV" and "high-kV" in order to emit low energy X-rays and high energy X-rays, respectively, from an X-ray tube. The high voltage generator may typically switch, for example, between a low-kV of about 70 to 100 kilovolts (kV) and a high-kV of about 120 to 150 kV. The low energy and high energy X-rays emitted, after being attenuated by the patient or object, impinge upon an array of radiation detectors. The intensity of the X-rays may then be processed to produce an image.

To complete a dual energy scan in a single rotation, the high voltage generator must rapidly switch between low-kV and high-kV. Such rapid switching may typically be performed between 10 µs and 30 µs, though even faster times may be desirable. However, the high voltage generator typically includes a high voltage (HV) capacitance which may include a filtering capacitor and/or parasitic capacitance (such as from high voltage cabling). As a result, the fall time between high-kV and low-kV is related to the discharge of the HV capacitance. In a typical CT system, the tube current may oftentimes be the largest part of the current resulting from discharge of the HV capacitance.

In CT, it is also often desirable to modulate tube current supplied by the high voltage generator in order to adjust the X-ray exposure for different parts of the body or differently sized objects. This helps to prevent overexposing or underexposing the patient or object during data acquisition.

However, modulating tube current during a dual energy scan, such as during a high-kV time, creates different (inconsistent) fall times between high-kV and low-kV from cycle to cycle. This, in turn, creates undesirable disproportionate energy separation between the energy amounts transferred during high-kV times and the energy amounts transferred during low-kV times. In other words, modulating tube current during dual energy scans may result in non-ideal waveforms which may impact the ability to effectively reconstruct scanned images.

In addition, the HV capacitance may vary in time, for example, as a function of temperature. This may also create different, inconsistent fall times, particularly as compared to any calibration which may have been done at a different temperature.

Therefore, it is desirable to provide an improved high voltage generator which provides a generally constant energy separation between high-kV and low-kV times during a dual energy scan in which tube current modulation is used. Moreover, it is desirable to provide an improved high voltage generator which may provide substantially identical energy separation between high-kV and low-kV times during a dual energy scan executed under differing environmental conditions.

BRIEF DESCRIPTION OF THE INVENTION

The present inventors have recognized that fall times between energy levels, such as between high-kV to low-kV levels (during a "dual energy" or "fast-kV" energy scan), or during a multi-energy scan, are linked to the discharge of HV (high voltage) capacitance. In an embodiment of the invention, a high voltage generator may be activated during fall transitions from first to second energy levels in order to substantially maintain a predetermined fall transition time. Accordingly, substantially equal energy distributions between high-kV and low-kV levels may be achieved such that a CT reconstruction algorithm can more effectively reconstruct scanned images.

Specifically then, the present invention, in one embodiment, may provide a control system for X-ray imaging. A high voltage generator may be configured to provide a first voltage level and a second voltage level for an X-ray source for providing an energy scan. An X-ray source may be configured to receive the first voltage level and the second voltage level. A controller may be in communication with the high voltage generator and the X-ray source. The controller may be configured to activate the high voltage generator to supply an equalization current to substantially maintain a constant fall time from the first voltage level to the second voltage level.

Also, a method for X-ray imaging may include: (a) providing a high voltage level and a low voltage level for providing an energy scan; (b) providing an X-ray source receiving the high voltage level and the low voltage level; and (c) supplying an equalization current to substantially maintain a constant fall time from the high voltage level to the low voltage level.

Also, a CT imaging system may include: a gantry; a high voltage generator configured to provide a first voltage level and a second voltage level for providing an energy scan; an X-ray source disposed on the gantry, the X-ray source configured to receive the first voltage level and the second voltage level; and a controller in communication with the high voltage generator and the X-ray source. The controller may be configured to activate the high voltage generator to supply an equalization current to modify a discharge of an HV capacitance to substantially maintain a constant fall time from the first voltage level to the second voltage level.

DETAILED DESCRIPTION OF THE INVENTION

Figure 1:
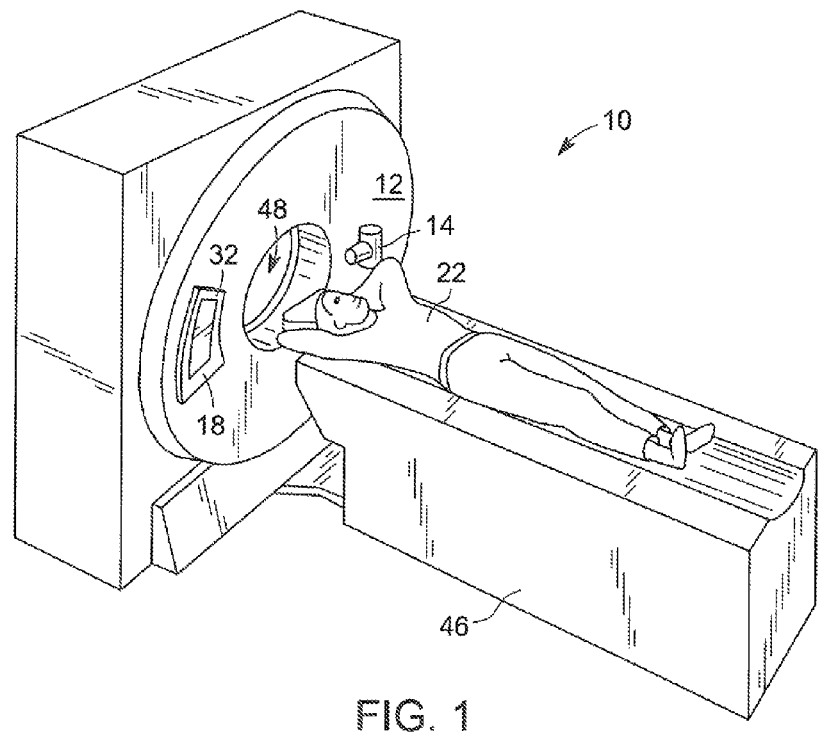
FIG. 1 is a pictorial view of an exemplar CT imaging system in accordance with an embodiment of the invention.
Figure 2:
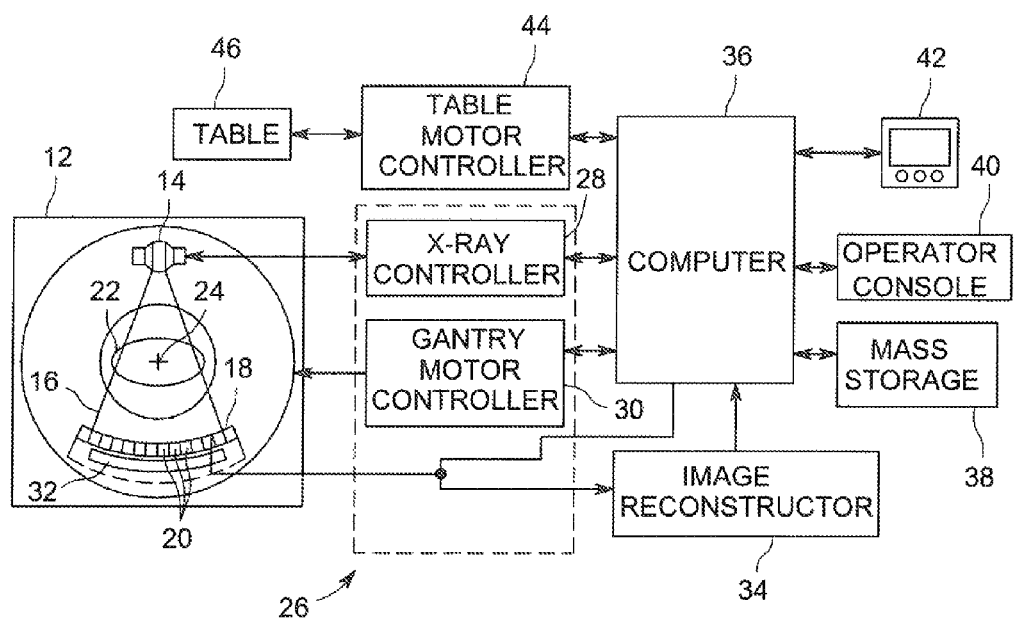
FIG. 2 is a block schematic diagram of the system illustrated in FIG. 1.

Referring now to FIG. 1, an exemplary computed tomography (CT) imaging system 10 is shown as including a gantry 12 which may be representative of a "third generation" CT scanner. The gantry 12 includes an X-ray source 14 which projects a polychromatic beam of X-rays 16 toward a detector assembly 18 on an opposite side of the gantry 12. Typically, a collimator may be an integral part of the detector assembly 18. Referring also to FIG. 2, the detector assembly 18 may be formed by a plurality of detectors 20 and data acquisition systems (DAS) 32. The plurality of detectors 20 sense the projected X-rays which pass through a patient 22 or object, and the DAS 32 converts corresponding data to digital signals for subsequent processing. Each detector 20 produces an analog electrical signal that represents the intensity of an impinging X-ray beam, and hence the attenuated beam as it passes through the patient 22. During a scan to acquire X-ray projection data, the gantry 12 and the components mounted thereon rotate about a center of rotation 24.

Rotation of the gantry 12 and the operation of X-ray source 14 are governed by a control mechanism 26 of CT system 10. The control mechanism 26 includes an X-ray generator system 28 that provides power and timing signals to an X-ray source 14 (X-ray tube) and a gantry motor controller 30 that controls the rotational speed and position of the gantry 12. An image re-constructor 34 receives sampled and digitized X-ray data from the DAS 32 and performs high speed reconstruction. The reconstructed image is applied as an input to a computer 36 which stores the image in a mass storage device 38.

The computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by the computer 36 to provide control signals and information to the DAS 32, the X-ray generator system 28 and the gantry motor controller 30. In addition, the computer 36 operates a table motor controller 44 which controls a motorized table 46 to position the patient 22 and the gantry 12. In particular, the motorized table 46 is operable to move the patient 22 through a gantry opening 48, as illustrated in FIG. 1, in whole or in part.

Figure 3:
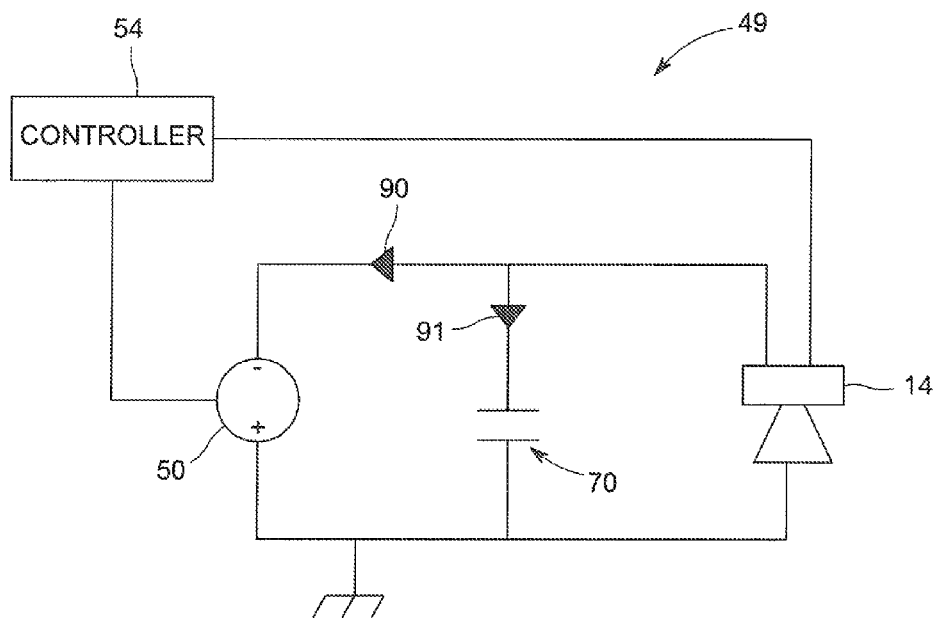
FIG. 3 is a simplified diagram of an X-ray generator system and X-ray source for the system of FIGS. 1 and 2.

Referring now to FIG. 3, a simplified diagram of a system 49 which includes an X-ray generator and X-ray source of the system of FIGS. 1 and 2 is illustrated. The system 49 includes a high voltage generator 50 (tube voltage) configured to provide power and timing signals to the X-ray source 14. The X-ray source 14, in turn, provides tube current generation which may be modulated. A controller 54, in communication with the high voltage generator 50 and the X-ray source 14, provides control with respect to tube voltage provided by the high voltage generator 50 and tube current provided by the X-ray source 14. The tube current may be modulated, for example, by changing the temperature of the filament of the X-ray source 14, and/or by modulating electrical fields within the X-ray tube.

Figure 5:
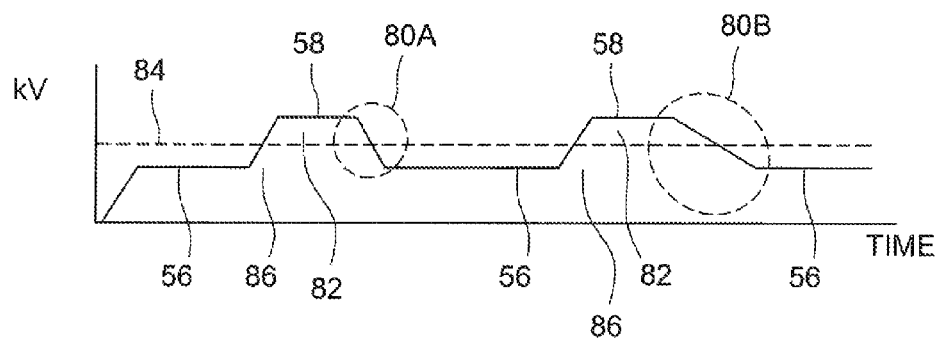
FIG. 5 is a graph illustrating an energy scan in which periodic switching between a low energy level (low-kV) and a high energy level (high-kV) with tube current modulation results in varying energy separations.

With additional reference to FIG. 5, by way of example, for a dual energy scan, the controller 54 may control the high voltage generator 50 to switch between a first voltage/energy level (low-kV) 56 and a second voltage/energy level (high-kV) 58 with respect to the X-ray source 14 in order to emit low energy X-rays and high energy X-rays, respectively, via the X-ray source 14. The high voltage generator 50 may typically switch, for example, between a low-kV of about 70 to 100 kilovolts (kV) and a high-kV of about 120 to 150 kV. Switching may also typically occur at frequencies ranging from 500 Hz to 25 KHz, with rise times typically ranging from 10 μs to 150 μs, and fall times typically ranging (depending on tube current) from 10 μs to 300 μs.

Figure 4:
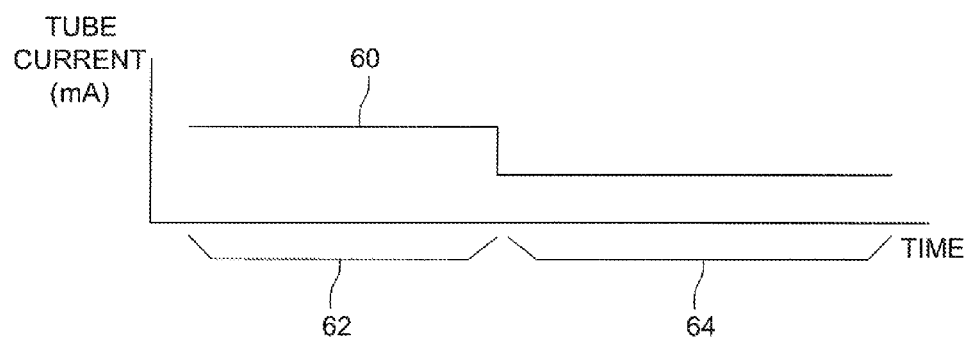
FIG. 4 is a graph illustrating tube current modulation from the X-ray generator system of FIG. 4.

To adjust the X-ray exposure, such as for different parts of the body or differently sized objects, the controller 54 may control the tube current via the X-ray source 14 to provide tube current modulation. With additional reference to FIG. 4, the X-ray source 14 may be controlled to modulate tube current (at a voltage/energy level in accordance with the high voltage generator 50). In particular, the X-ray source 14 may be controlled to release electrons in varying amounts, based on varying control of the heated filament, and/or through electrodes used to modulate electric fields within the X-ray tube 14. Such tube current modulation may help to prevent, for example, overexposing or underexposing the patient 22 during data acquisition.

To complete a dual energy scan in a single rotation, the controller 54 controls the high voltage generator 50 to rapidly switch between the first voltage/energy level (low-kV) 56 and the second voltage/energy level (high-kV) 58. At certain times, the controller 54 also controls the X-ray source 14 to modulate the tube current between different tube currents. For example, with reference to FIGS. 4 and 5 together, for a broader cross-sectional area of the patient 22, the high voltage generator 50 may switch between the first voltage/energy level (low-kV) 56 and the second voltage/energy level (high-kV) 58 (perhaps numerous times) during a first period 62 while the X-ray source 14 is controlled to provide the tube current at a first (greater) amount. Then, for a narrower cross-sectional area of the patient 22, the high voltage generator 50 may continue to switch between the first voltage/energy level (low-kV) 56 and the second voltage/energy level (high-kV) 58 (perhaps numerous times) during a second period 64 while the X-ray source 14 is controlled to provide the tube current at a second (lesser) amount.

Referring back to FIG. 3, the system 49 also includes a high voltage (HV) capacitance 70 with respect to the X-ray source 14. The HV capacitance 70 may represent a filtering capacitor and/or parasitic capacitance (such as from high voltage cabling).

With reference again to FIG. 5, the present inventors have recognized that fall times 80a and 80b between high-kV and low-kV are linked to the discharge of HV capacitance 70 during tube current modulation. For example, in a first fall time 80a, in which the X-ray source 14 is controlled to provide the tube current at a first (greater) amount, the first fall time 80a may have a faster fall time (steeper slope). However, in a second fall time 80b, in which the X-ray source 14 is controlled to provide the tube current at a second (lesser) amount, the second fall time 80b may have a slower fall time (gradual slope). These different (inconsistent) fall times create undesirable disproportionate energy separation between energy amounts transferred during high-kV times 82 (above a low-kV to high-kV separation midpoint 84) and energy amounts transferred during low-kV times 86 (below the low-kV to high-kV separation midpoint 84).

In order to provide substantially equal energy separation between energy amounts transferred during high-kV times and energy amounts transferred during low-kV times, the high voltage generator 50 is activated during faster fall times, such as the first fall time, to supply an equalization current 90 to modify or slow a discharge of the HV capacitance 70 with a high voltage capacitance current 91. The equalization current 90 may be provided by supplying a portion of the tube current via the high voltage generator 50. By supplying the equalization current 90 to slow discharge of the HV capacitance 70, faster fall times, such as the first fall time 80a, may be slowed down to be consistent with slower fall times, such as the second fall time 80b. As used herein, "equalization" refers to an amount of current sufficient to slow discharge of the HV capacitance 70 in order to equalize the fall times 80a and 80b to be substantially constant between cycles. Preferably, the equalization current 90 equalizes the fall times 80a and 80b to a maximum fall time 80b which may correspond to a minimum value of the tube current.

Figure 6:
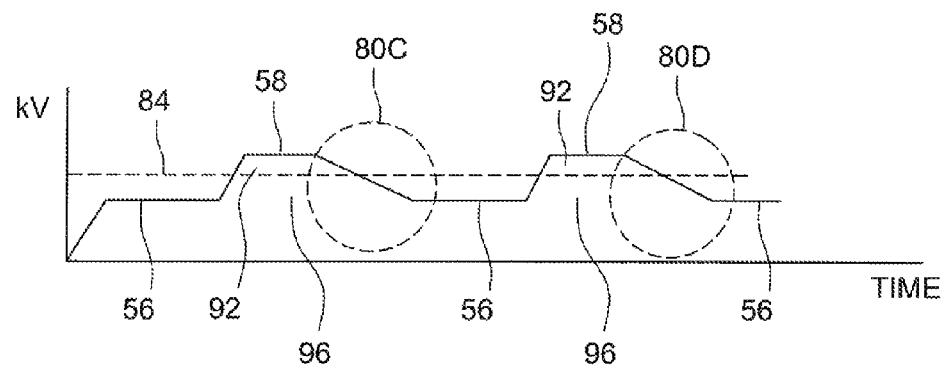
FIG. 6 is a graph illustrating an energy scan in which the X-ray generator system of FIG. 5 is controlled to periodically switch between a low energy level (low-kV) and high energy level (high-kV) with tube current modulation to generally maintain constant energy separation in accordance with an embodiment of the invention.

Referring now to FIG. 6, in a third fall time 80c (which may correspond to the tube current providing a greater amount of the current), the high voltage generator 50 is activated to supply the equalization current 90 to modify or slow a discharge of the HV capacitance 70. Then, in a fourth fall time 80d (which may correspond to the tube current providing a lesser amount of the current, and preferably a minimum amount of the current) the high voltage generator 50 does not supply the equalization current 90. However, as a result of the high voltage generator 50 supplying the equalization current 90 in the third fall time 80c, the third fall time 80c is slowed to substantially match the fourth fall time 80d. Consequently, the high voltage generator 50 is controlled to supply the equalization current 90 at times to substantially maintain a constant fall time. As a result, the technical effect is to provide substantially equal energy separation between energy amounts transferred during high-kV times 92 (above a low-kV to high-kV separation midpoint 84) and energy amounts transferred during low-kV times 96 (below the low-kV to high-kV separation midpoint 84).

Figure 7:
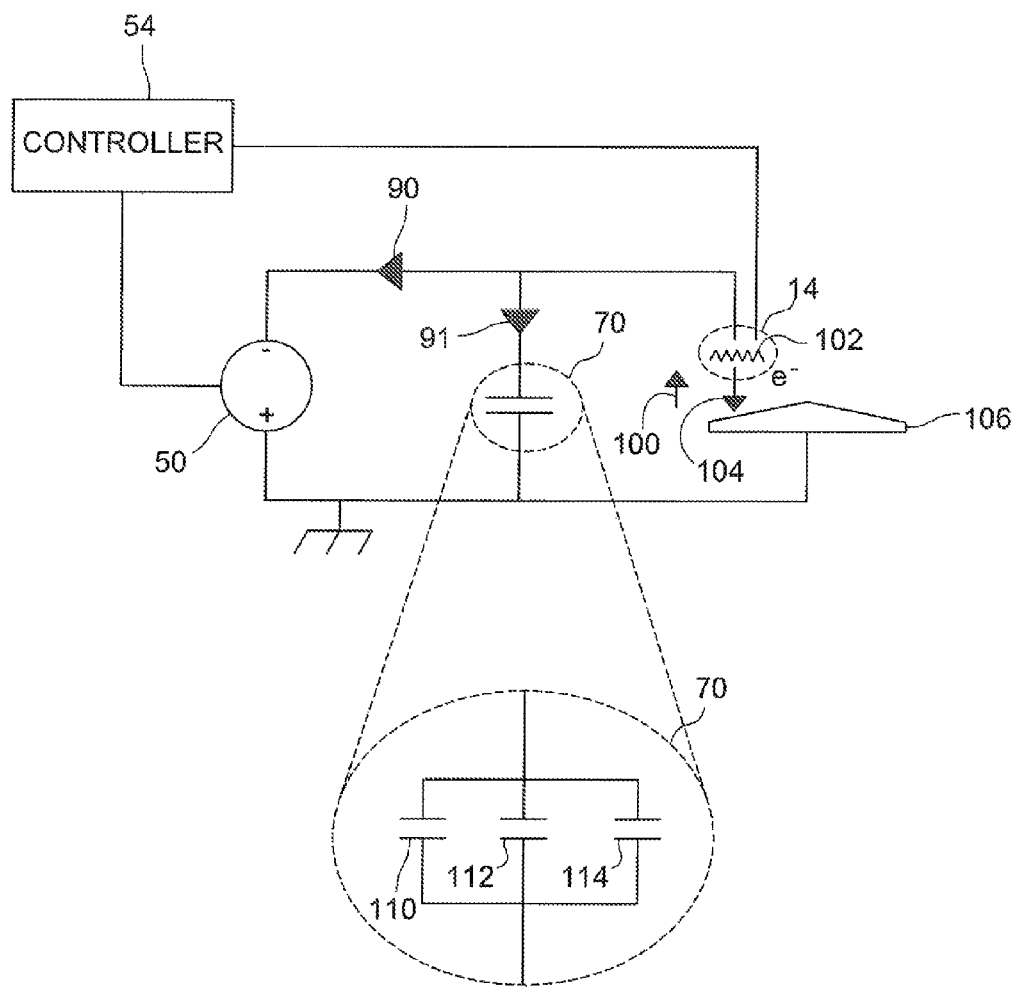
FIG. 7 is a simplified schematic of the X-ray generator system and X-ray source of FIG. 3.

Referring now to FIG. 7, a simplified schematic of the X-ray generator system and X-ray source of FIG. 3 is provided. For a dual energy scan, the controller 54 controls the high voltage generator 50 to switch between a first voltage/energy level (low-kV) 56 and a second voltage/energy level (high-kV) 58 with respect to the X-ray source 14 in order to emit low energy and high energy X-rays, respectively, via the X-ray source 14. The high voltage generator 50 may typically switch, for example, between a low-kV of about 70 to 100 kilovolts (kV) and a high-kV of about 120 to 150 kV. Switching may also typically occur at frequencies ranging from 500 Hz to 25 KHz, with rise times typically ranging from 10 μs to 150 μs, and fall times typically ranging (depending on tube current) from 10 μs to 300 μs.

To adjust the X-ray exposure, such as for different parts of the body or differently sized objects, the controller 54 may control the X-ray source 14 to provide tube current modulation. The X-ray source 14, in turn, modulates tube current 100 (at a voltage/energy level in accordance with the high voltage generator 50). In particular, an X-ray tube filament 102 of the X-ray source 14 may release electrons 104 in varying amounts, based on varying control of the filament 102, toward an X-ray tube anode 106. Such tube current modulation may help, for example, to reduce X-ray exposure to the patient 22 during data acquisition.

The high voltage (HV) capacitance 70 may include a high voltage generator capacitance 110 (resulting from the high voltage generator 50), a high voltage cable capacitance 112, and/or a high voltage tube capacitance 114 (resulting from the X-ray source 14). Additional filtering capacitance for filtering the low-kV and high-kV may also be included.

Alternative aspects of the invention may include providing energy scans with more than two energy levels. For example, the high voltage generator could similarly be activated during a fall transition from a third energy level (high-kV') to a second energy level (high-kV), from a fourth energy level (high-kV'") to the third energy level (high-kV'), and so forth. Such activations of the high voltage generator may allow maintaining the predetermined fall transition times between the respective energy levels. Also, predetermined fall transition times may be achieved according to aspects of the invention without tube current modulation, such as to reduce calibration requirements. These alternative aspects are within the scope of the present inventions.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A control system for X-ray imaging comprising:
a high voltage generator configured to provide at least a first voltage level and a second voltage level for providing an energy scan;
an X-ray source configured to receive the first voltage level and the second voltage level to emit low energy and high energy X-rays, respectively; and
a controller in communication with the high voltage generator and the X-ray source,
wherein the controller is, configured to modulate a tube, current of the X-ray source to adjust X-ray exposure while switching the high voltage generator between the first voltage level and the second voltage level, and
wherein the controller is configured to activate the high voltage generator to supply an equalization current to slow a discharge of a high voltage (HV) capacitance, while the X-ray source provides the tube current, to substantially maintain a constant fall time from the first voltage level to the second voltage level.

2. The control system of claim 1, wherein the constant fall time is determined according to a fall time in which the X-ray source provides a minimum value of the tube current.

3. The control system of claim 1, wherein the HV capacitance includes a high voltage cable capacitance.

4. The control system of claim 1, wherein the HV capacitance includes a high voltage generator capacitance and a high voltage tube capacitance.

5. The control system of claim 1, wherein the first voltage level is greater than 120 kV.

6. The control system of claim 1, wherein the second voltage level is less than 100 kV.

7. The control system of claim 1, wherein the high voltage generator provides a third voltage level and the controller is configured to activate the high voltage generator to supply the equalization current to substantially maintain a constant fall time from the third voltage level to the second voltage level.

8. A method for X-ray imaging comprising:
providing a first voltage level and a second voltage level for providing an energy scan;
providing an X-ray source receiving the first voltage level and the second voltage level to emit low energy and high energy X-rays, respectively;
modulating a tube current of the X-ray source to adjust X-ray exposure while switching between the first voltage level and the second voltage level; and
supplying an equalization current to slow a discharge of a high voltage (HV) capacitance, while the X-ray source provides the tube current, to substantially maintain a constant fall time from the first voltage level to the second voltage level.

9. The method of claim 8, further comprising determining the constant fall time according to a fall time in which a minimum value of the tube current is provided.

10. The method of claim 8, wherein the HV capacitance includes a high voltage cable capacitance.

11. The method of claim 8, wherein the HV capacitance includes a high voltage generator capacitance and a high voltage tube capacitance.

12. The method of claim 8, further comprising providing a third voltage level and supplying an equalization current to substantially maintain a constant fall time from the third voltage level to the second voltage level.

13. A CT imaging system comprising:
a gantry;
a high voltage generator configured to provide a first voltage level and a second voltage level for providing an energy scan;
an X-ray source disposed on the gantry, the X-ray source configured to receive the first voltage level and the second voltage level t emit low energy and hub energy X-rays, respectively; and
a controller in communication with the high voltage generator and the X-ray source,
wherein the controller is configured to modulate a tube current of the X-ray source to adjust X-ray exposure while switching the high voltage generator between the first voltage level and the second voltage level, and
wherein the controller is configured to activate the high voltage generator to supply an equalization current to slow a discharge of an HV capacitance, while the X-ray source provides the tube current, to substantially maintain a constant fall time from the first voltage level to the second voltage level.

14. The CT imaging system of claim 13, wherein the constant fall time is determined according to a fall time in which the X-ray source provides a minimum, value of the tube current.

15. The CT imaging system of claim 13, wherein the HV capacitance includes a high voltage cable capacitance.

16. The CT imaging system of claim 15, wherein the HV capacitance includes a high voltage generator capacitance and a high voltage tube capacitance.

\* \* \* \* \*

UNITED STATES PATENT AND TRADEMARK OFFICE
CERTIFICATE OF CORRECTION

PATENT NO. : 9,970,889 B2  
APPLICATION NO. : 14/658913  
DATED : May 15, 2018  
INVENTOR(S) : Jean-Francois Larroux et al.

Page 1 of 1

It is certified that error appears in the above-identified patent and that said Letters Patent is hereby corrected as shown below:

In the Claims

Claim 1, Column 6, Line 48, after "is" delete ",";

Claim 1, Column 6, Line 48, after "tube" delete ",";

Claim 13, Column 8, Line 10, after "level" delete "t" and substitute therefore -- to --;

Claim 13, Column 8, Line 10, delete "hub" and substitute therefore -- high --;

Claim 14, Column 8, Line 24, after "minimum" delete ",".

Signed and Sealed this  
Twenty-sixth Day of June, 2018

Andrei Iancu  
*Director of the United States Patent and Trademark Office*